(12) United States Patent
Grez

(10) Patent No.: US 8,037,566 B2
(45) Date of Patent: Oct. 18, 2011

(54) POWER TOOTHBRUSH USING ACOUSTIC WAVE ACTION FOR CLEANSING OF TEETH

(75) Inventor: Joseph W. Grez, North Bend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 861 days.

(21) Appl. No.: 11/722,975

(22) PCT Filed: Apr. 7, 2005

(86) PCT No.: PCT/IB2005/051148
§ 371 (c)(1), (2), (4) Date: Nov. 23, 2007

(87) PCT Pub. No.: WO2006/070296
PCT Pub. Date: Jul. 6, 2006

(65) Prior Publication Data
US 2008/0155770 A1    Jul. 3, 2008

(51) Int. Cl.
*A61C 17/20* (2006.01)
*A61C 17/22* (2006.01)

(52) U.S. Cl. ......... 15/22.1; 433/118; 433/119; 601/142; 601/46

(58) Field of Classification Search .......... 15/22.1, 15/110; 433/119, 118; 601/142, 46
See application file for complete search history.

(56) References Cited

U.S. PATENT DOCUMENTS

| | | | |
|---|---|---|---|
| 4,127,125 A | 11/1978 | Takemoto et al. | |
| 4,813,403 A * | 3/1989 | Endo | 601/46 |
| 4,913,133 A | 4/1990 | Tichy | |
| 5,255,274 A * | 10/1993 | Wysocki et al. | 372/26 |
| 5,314,333 A * | 5/1994 | Irmer et al. | 433/120 |
| 5,378,153 A | 1/1995 | Giuliani et al. | |
| 5,531,598 A | 7/1996 | Rosenberg et al. | |
| 5,546,624 A * | 8/1996 | Bock | 15/22.1 |
| 5,730,594 A | 3/1998 | Sharp | |
| 6,202,241 B1 | 3/2001 | Hassell et al. | |

FOREIGN PATENT DOCUMENTS

| | | |
|---|---|---|
| EP | 0 893 106 | 1/1999 |
| JP | 10165228 A * | 6/1998 |
| JP | 2004148079 A * | 5/2004 |
| WO | 9210146 | 6/1992 |

* cited by examiner

*Primary Examiner* — Shay Karls
(74) *Attorney, Agent, or Firm* — Daniel Sheridan

(57) ABSTRACT

The toothbrush includes a handle portion and a brushhead assembly which comprises a head portion and a stem portion. The head portion includes a bellows-like acoustic action member for creating acoustic wave action as it moves in and out in response to an acoustic driving force. A drive system is located in the handle and includes an audio speaker-type assembly to create acoustic waves which are transmitted through a transmission line to the acoustic action member. The acoustic action member is driven toward and away from the teeth when the toothbrush is operatively positioned within the mouth. The action of the acoustic member is directly or indirectly coupled to the fluid in the mouth, producing a foam which couples shear forces between the acoustic action member and the teeth/gums to produce a desired cleaning/therapeutic effect.

15 Claims, 6 Drawing Sheets

POWER TOOTHBRUSH USING ACOUSTIC WAVE ACTION FOR CLEANSING OF TEETH

RELATED APPLICATIONS

This is a continuation-in-part of PCT application No. IB2004/051013, filed on Jun. 25, 2004, which designated the United States of America.

CROSS REFERENCE TO RELATED APPLICATION

This application claims the benefit of U.S. application Ser. No. 11/022,910 filed 27 Dec. 2004, which is incorporated herein by reference.

TECHNICAL FIELD

This invention relates generally to power toothbrushes, and more specifically concerns power toothbrushes which use acoustic wave action to produce a cleansing effect for the teeth of the user.

BACKGROUND OF THE INVENTION

In general, power toothbrushes for cleaning teeth, including plaque removal, are well known. Typically, such power toothbrushes rely on a set of bristles attached to a bristle mounting plate which is moved by a driver to scrub the surfaces of the teeth. There are various known bristle configurations which are designed to effectively scrub exposed surfaces on the teeth, as well as to reach to some extent between the teeth or just under the gum line. Such brushing devices which rely on the scrubbing action of bristles for cleaning typically require significant pressure exerted by the user against the teeth to accommodate the differences in the shapes of the various teeth and to effectively clean the teeth. However, such pressure exerted against the teeth by the bristles typically results in a significant abrasion effect, including damage to both the soft and hard tissues in the mouth. This is of course undesirable, but often unavoidable to obtain the desired cleansing.

There are also limitations on the size (length and diameter) of the bristles insofar as while a small size may be desirable to reach between the teeth and under the gum line, the bristles still must be stiff enough to effectively scrub the teeth. Hence, with respect to a bristle-type toothbrush, effective cleaning is important but it is also desirable that as light a pressure as possible on the bristles be used, to reduce abrasion and tissue damage.

In addition, ultrasonic energy is used, either alone, or in addition to bristle action, to clean plaque from teeth. However, the level of ultrasonic energy used in the mouth is typically too low to be effective for plaque removal if reasonable safety is to be maintained.

Still other toothbrushes, particularly those using a resonant system, produce some degree of acoustic action by moving fluids in the mouth by the action of the moving bristles at the resonant frequency of the toothbrush. However, the resonant frequency of such a toothbrush is typically not the most effective frequency for all areas of the mouth. Further, the acoustic effect of such devices, produced by the bristle action, is typically not sufficient by itself to produce a clinically effective cleansing action. Such devices still rely to a significant extent on the scrubbing action of the bristles for cleaning.

The fact that the bristles themselves create the limited acoustic effect described above is significant relative to the effectiveness of the acoustic action. Increasing the amount of acoustic energy generated, in order to make that portion of the cleansing action more effective, will result in increased bristle motion and tissue abrasion. Further, providing additional power to increase the acoustic effect will result in additional bulk and cost to the device.

Hence, it is desirable to have a toothbrush which effectively cleans teeth, including the hard to reach areas, such as between the teeth and under the gum line, which relies primarily on acoustic action not produced by bristle movement.

SUMMARY OF THE INVENTION

Accordingly, the present invention is a power toothbrush which includes a handle portion, a head portion, the head portion containing a member for creating acoustic action outwardly from the head portion, acting on fluid in a user's mouth; and a drive system for moving the acoustic member relative to the teeth, such that when the head portion is operatively positioned in the mouth of a user, the acoustic member moves toward and away from the teeth of the user, wherein movement of the acoustic member causes an acoustic wave action on fluid contacting the teeth, producing a cleansing effect on the teeth.

BEST MODE FOR CARRYING OUT THE INVENTION

In general, the present invention is an acoustic power toothbrush, that is, a power toothbrush which produces acoustic wave action in the sonic frequency range, typically less than 1 KHz, which when operatively positioned in the mouth, either directly or indirectly activates the fluid in the mouth to produce an acoustic cleaning action on the teeth of the user. Typically, the acoustic action is effective on the exposed surfaces of the teeth, as well as between the teeth and below the gum line. The acoustic action is produced by a non-bristled acoustic cleansing member, such as a bellows diaphragm made from flexible material such as rubber, or an equivalent member, as opposed to bristles, although bristles can be used as a boundary, i.e. partially surrounding the diaphragm, to enhance the acoustic action of the toothbrush or to contain the acoustic action to a particular volume, i.e. region, of the mouth, covering selected teeth adjacent the acoustic member. The bristles could also be configured to serve as a distance element for proper standoff between the membrane and the teeth during operation of the device. A wall element could be used for this purpose as well. The bristles or wall element can also assist in focusing of fluid flow to the teeth.

As disclosed in more detail below, in one embodiment, an acoustic system driver can be positioned in a handle portion of the toothbrush, with the driving energy transmitted up to a head portion of the toothbrush, where it acts on the acoustic cleansing member, or the acoustic system driver and the acoustic cleansing member can be contained entirely in the head portion of the toothbrush.

Figure 1:
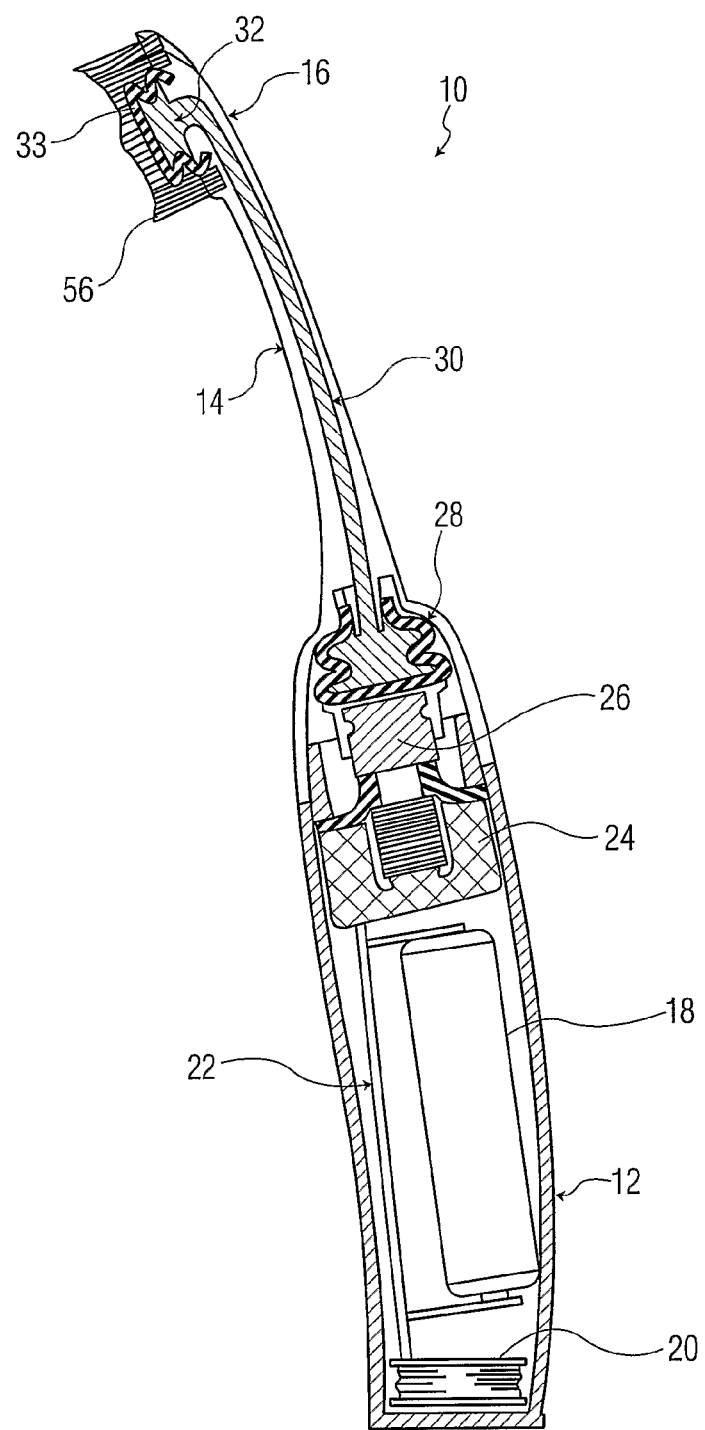
FIG. 1 is a cross-sectional diagram showing one embodiment of the acoustic toothbrush of the present invention.

Referring now specifically to FIG. 1, a first embodiment of the acoustic toothbrush of the present invention is shown generally at 10. The toothbrush includes a handle 12, a stem portion 14 and a head portion 16. The combination of the stem 14 and the head portion 16 is also referred to as a brushhead assembly. In handle 12 is a conventional battery 18, a charging coil 20 to periodically charge the battery 18, and an electronic control and drive circuit, including a control microprocessor, shown generally at 22. The handle also includes the acoustic system driver which is similar in structure and operation to a high powered audio speaker. Generally, the acoustic system driver is capable of supplying at least a few watts of power for the acoustic cleansing member in the head portion of the toothbrush.

The acoustic system driver includes a magnet 24 and a voice coil 26, such as might be part of a conventional audio speaker. The acoustic system driver is controlled by drive signals produced by electronic circuit 22. The acoustic system driver also includes a speaker diaphragm, in this embodiment a bellows 28, to produce the acoustic waves. Typically, the frequency of the acoustic waves from the bellows 28 will be in the range of 20 Hz to 300 Hz, with 250-260 Hz being generally preferred. Frequencies up to 1000 Hz are possible, however. The control circuit 22 has the capability of storing and providing different driving frequencies, so that different individual frequencies can be selected during operation of the toothbrush, as well as a combination of frequencies. In this way, the frequency of the acoustic wave action can be matched to particular areas of the mouth or different cleansing actions can be provided, as discussed in more detail below.

The acoustic waves produced off of bellows diaphragm 28 is directed to an acoustic transmission line 30 which extends through the stem portion 14 of the toothbrush. The transmission line 30 can be, for instance, a fluid-filled tube, an air-filled tube, or even a mechanical actuator arm which transmits the acoustic action/energy. The fluid in the transmission line for instance could be a natural oil, which provides little if any opportunity for bacterial growth, even in the event of a pinhole opening in the line. Water-based materials may also be used with additives to prevent bacterial growth. The transmission line 30 transmits the acoustic energy produced by the drive system to an acoustic action member in head portion 16 of the toothbrush, typically in the form of a flexible acoustic cleansing member 32, also referred to as an acoustic action member, which in the embodiment shown is a bellows. The acoustic action bellows is driven in and out by the acoustic drive energy from the fluid in the transmission line, producing acoustic waves off a front surface 33 thereof.

Figure 3:
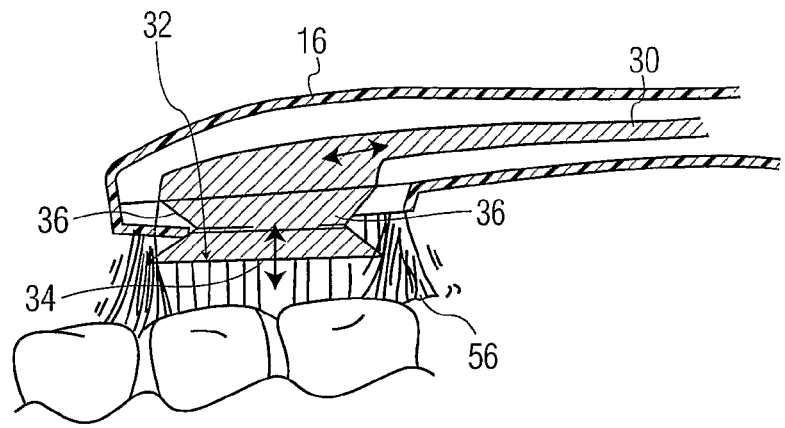
FIG. 3 is a cross-sectional view showing in more detail a portion of the toothbrush in FIG. 1.

FIG. 3 shows additional detail of the acoustic action bellows 32. It is made from a flexible material, such as rubber, which is capable of moving toward and away from the teeth when the toothbrush is properly oriented in the mouth, in response to the acoustic drive energy from the drive system in the handle. Generally, acoustic bellows 32 includes a front flat portion 34 and a peripheral edge portion 36 which moves between a concave configuration, such as shown in FIG. 3, and a straighter, extended configuration, during which time the front portion 34 moves toward the teeth. The bellows arrangement permits a lower peristaltic volume as well as a convenient means for moving the acoustic member close to the teeth. In operation, the front portion will move a maximum of 5 mm and a minimum of 0.5 mm in response to the drive system action to produce the acoustic cleaning action.

While the flexible bellows-type element 32 provides good results, a solid piston like member or a paddle could alternatively be used. Typically, the acoustic action member will move toward and away from, in some cases approximately at right angle to, the teeth, producing acoustic wave action necessary for effective cleansing of the teeth.

This physical action by the acoustic action member 32 (bellows) will be coupled to the fluid within the mouth either directly, meaning that the front portion 34 of the bellows contacts the fluid directly, or indirectly (through air or an impedance matching material), in which an acoustic wave is produced which in turn affects the fluids in the mouth to produce an acoustic effect.

The fluids in the mouth, under the influence of the acoustic action produced by the bellows 32, produces a desired cleansing action for the teeth which is clinically effective. The front portion of the acoustic member can be configured in various ways other than flat. The action on the fluid will typically create a significant amount of foam, with the foam, driven by the acoustic action, producing significant cleansing effects for the teeth.

This is accomplished by what is referred to herein as acoustic action, which generally refers to the transmission of wave action in a medium, such as foam, that flows with a speed within the sound range and has a particular density. The medium molds to surfaces within the mouth and on the generating membrane, so that shear forces can be transmitted in the mouth from the membrane to the oral surfaces, with desired cleansing effects.

Foam is created from air and fluid in the mouth. The creation of foam is dependent to some extent on frequency, with lower frequencies producing larger bubbles and higher frequencies creating smaller bubbles. A frequency range of 100-700 Hz will likely be effective for the acoustic frequency. Plaque is removed from hard tooth surfaces by foam shear action. The moving foam, or liquid with a little foam, will force the biofilm away from the tooth surfaces.

Interproximal cleaning occurs by oscillating foam bubbles producing a cleansing action, with pressure oscillations creating expansion and contraction of foam bubbles in liquid. Cleaning has been shown to occur significantly at the liquid/bubble interface. Cleaning also occurs below the gum line, due to gingival pockets being vibrated open and closed to cause flow of oxygenated foam into those areas to oxygenate and then kill anaerobic bacteria. Both high and low frequencies (the range of 100-700 Hz) are effective to produce pocket movement (lower frequencies) and oxygenated foam (higher frequencies).

Figure 5A:
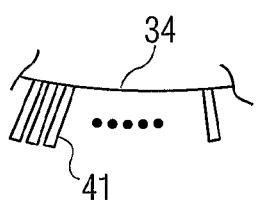
FIGS. 5A-5B show surface additions to the embodiment of FIG. 1 or FIG. 4 to accomplish direct engagement of the teeth.
Figure 5B:
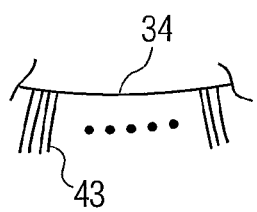

The front portion 34 of the bellows could have various configurations/arrangements, including smooth rubber, rubber fingers extending therefrom, or individual conventional or rubber bristles, as shown in FIGS. 5A and 5B. Typically, rubber fingers 41 will be approximately 5 mm long and 1.8 mm in diameter, while the conventional bristles 43 will be approximately 10 mm long and 0.15 mm in diameter. The front portion 34 could also have various surface configurations, including focusing arrangements to provide different acoustic effects into the fluid.

Figure 2:
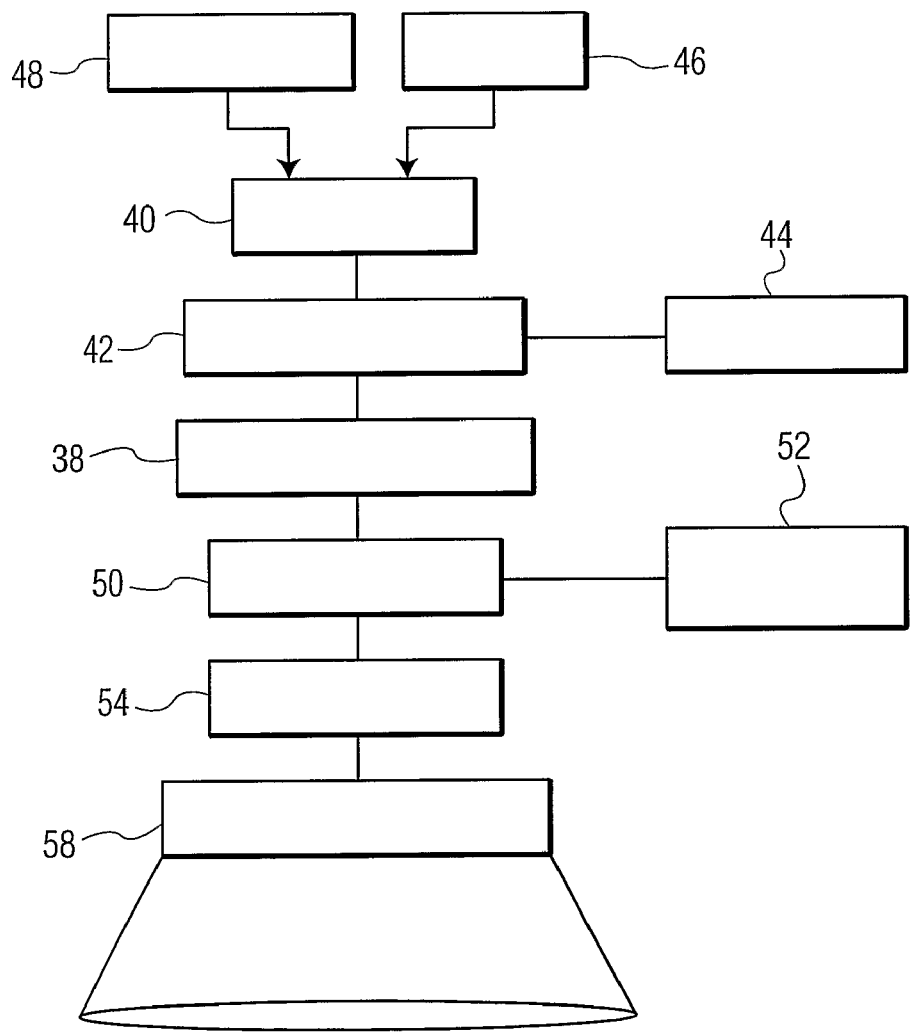
FIG. 2 shows a functional block diagram of the operation of the toothbrush of FIG. 1.

FIG. 2 shows the functional operation of the acoustic toothbrush of the present invention. In the electronic circuit 22 is a drive signal recorder (storage) 38. The drive signal recorder is capable of storing a plurality of acoustic drive signals or waveforms of different frequencies. Alternatively, the waveforms could be generated by an analog device/circuit. In a typical case, five to ten preprogrammed waveforms may be available, with the capability of storing additional waveforms, such as may be provided by a dental professional. These driving waveforms can be a single frequency, for instance, which may be matched with particular tissues in various portions of the mouth, such as the gums or different sections of the teeth, or they can be a particular combination of frequencies to produce different specific desirable effects in the mouth, including those frequencies or combinations of frequencies which are effective for gum massage, or various kinds of cleansing action, such as subgingival cleaning, which, as explained above, could be effective through the use of a lower frequency (approximately 200 Hz) to open up the pockets and a higher frequency (approximately 400 Hz) to produce the cleansing foam action to kill the bacteria in the pockets.

Thus, one significant advantage to the system of the present invention is the variety of frequencies available to produce various cleansing/treatment/therapeutic action for the teeth and gums.

A conventional charge coil and charge controller 40 and 42, respectively, charge the conventional batteries 44 which power the toothbrush. Charge coil 40 is responsive to a conventional charging device 46 in which the toothbrush may be positioned when not in use. Additional program information, such as additional drive frequencies, or combinations thereof, can be provided, at block 48, through charge coil 40 to the drive signal recorder 38. A microprocessor 50, with a resonator 52, which can be of various materials such as ceramic, or a crystal or an LRC circuit, controls the application of the drive signals to the speaker elements, and is responsive to commands from the user for a particular program or selection of frequencies.

Microprocessor 50 controls a conventional audio amplifier 54, the output of which drives the audio driver (speaker portion) 58 of the system. Referring to FIG. 1, the acoustic effect from the speaker 58 is then coupled via the transmission line 30 to the acoustic action member 32 in the head portion of the toothbrush.

The acoustic action member 32, such as the bellows in FIG. 1, can be used by itself or it can be surrounded or partially surrounded by a line of bristle tufts 56. The line of bristles 56 can be conventional nylon bristles, or they can be rubber bristles. While the line of bristles 56 is not necessary to the acoustic cleansing action they can enhance the overall effect, for instance, by forming at least a partial boundary for the acoustic fluid/foam produced by the bellows member. Hence, the bristles can act as a volume containment for the fluid action relative to particular teeth. Further, the bristles may provide position information back to the user.

In addition, the fluid action produced by the acoustic action member 32 can produce a movement of the bristles, or the acoustic action member can be arranged so that the movement thereof acts on the bristles directly, moving them to a certain extent, such as a range of movement of approximately 5 mm. The bristles will move in phase with the pressure waves created by the acoustic member, such that there is a bristle cleaning effect (scrubbing) in addition to the acoustic cleaning effect. In this way, a combined cleansing action is obtained. Further, the bristles may be mounted on the flexible portion of the bellows, such that the bristles are forced to move with the bellows, providing an increased bristle cleaning action as part of the total cleaning effect.

Figure 4:
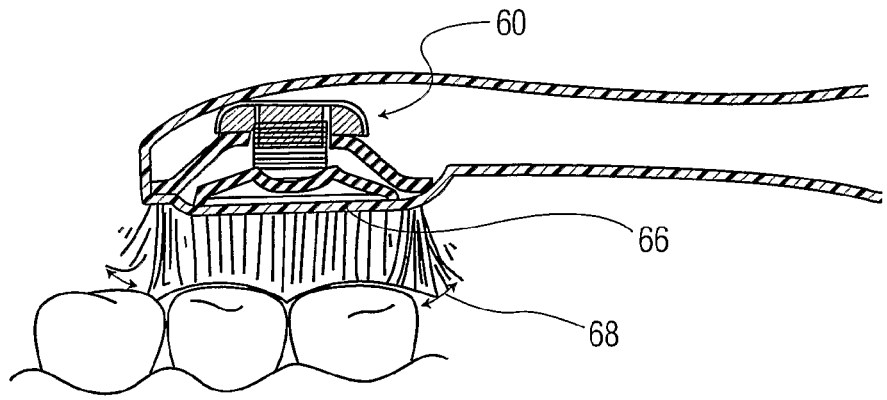
FIG. 4 is a cross-sectional view showing another embodiment of the toothbrush of the present invention.

Referring to FIG. 4, another embodiment of the present invention is shown in which the entire acoustic assembly is provided in a head portion of the toothbrush. In this arrangement, there is no fluid transmission line through the stem of the toothbrush. The audio speaker assembly is shown generally at 60, which in the above embodiment is in the handle of the toothbrush. The speaker assembly 60 includes a front diaphragm or membrane 66 which moves (0.5 mm-5 mm) in response to the speaker being driven by an energizing or drive signal from a driver circuit (not shown). The action of membrane 66 produces the desired acoustic wave action which is coupled to the fluid in the mouth, producing the foam which in turn couples shear force from the membrane 66 to the teeth or other oral cavity member, such as the gums. This embodiment may be advantageous in certain situations, but it has the disadvantages of a larger head size and generally less power. It should be understood that bristles 68 could also be used with this embodiment, surrounding the moving membrane, with similar effect and purpose to that shown and described above in the embodiment of FIG. 1.

Figure 6:
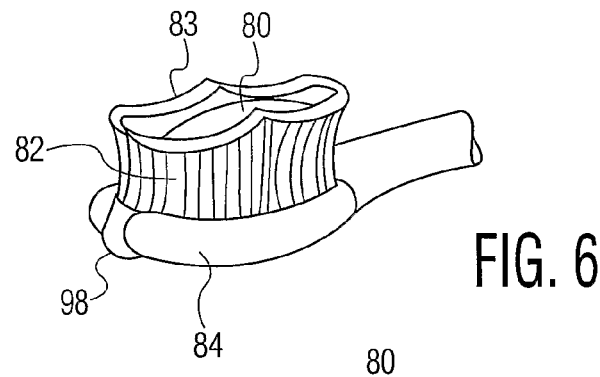
FIGS. 6-8 show various views of another embodiment of the present invention.
Figure 7:
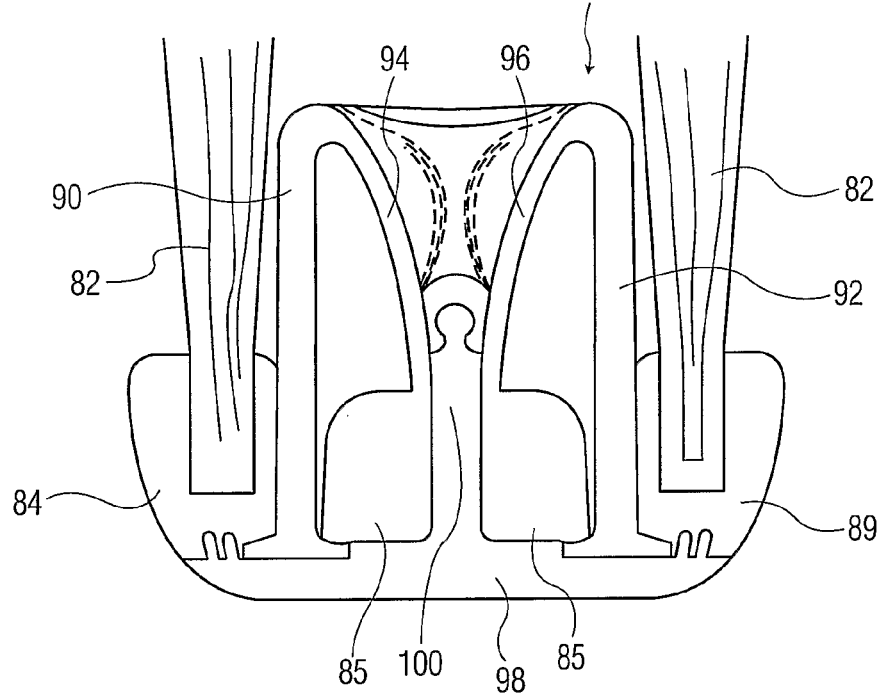
Figure 8:
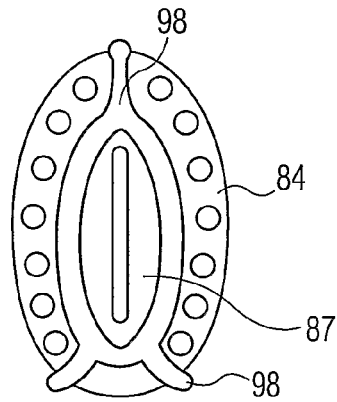

FIGS. 6-8 show another embodiment of the present invention. In this embodiment, a central flexible member, such as a membrane, 80 is substantially surrounded by a set of conventional bristle tufts 82. The bristle tufts are positioned, generally by stapling, in a plastic bristle holder member 84. The bristle tufts are scalloped at the upper edge 83 thereof, as shown in FIG. 6, to fit closely around adjacent teeth and slightly into the interproximal area between the teeth.

Positioned in the center area 87 of the brush is a flexible member or membrane 80, generally in the shape of ah "M". Flexible member 80 includes two substantially vertical outside wall portions 90 and 92 and two slightly curved convex inner wall portions 94 and 96. Member 80 and bristle holder member 84 are supported by an overmold member 98 into which they are snapped or otherwise mounted during manufacture. Overmold member 98 forms a base for the brush and includes an upstanding central rib 100 which extends down the center of the brush for a substantial portion of its length. The two inner portions 94 and 96 are connected at their lower ends to rib portion 100.

Surrounding rib 100 over a substantial portion of its length and to the outside wall portions 90 and 92 of the member 80 is an additional bristle holder member 85. The outside wall portions 90 and 92 are relatively thick, approximately 60/1000s inches, while the inner portions are approximately 20/1000s thick. Member 80 is driven so that the outer wall portions 90 and 92 thereof move outwardly a selected distance while the inner wall portions 94 and 96 move inwardly toward each other and somewhat in the direction of the teeth, as shown by the dotted lines in FIG. 7. The outside wall portions 90 and 92 are in contact with the bristle holder member 84, which substantially surrounds flexible member (membrane) 80, providing a back and forth motion toward and away from the member 80. The movement of the inner wall portions 94 and 96 produce a fluid jet along a center line of the toothbrush outward from the toothbrush in the direction of the teeth.

The fluid is squeezed outwardly toward the teeth in a repetitive manner by action of the membrane to produce a stream of fluid droplets toward the gum line and the interdental spaces.

The back and forth action of the bristles 82 produces a cleansing action on the face of the teeth, in particular the accessible areas of the teeth. The action of the flexible member with the fluid jet produces cleansing in the inter-proximal areas and gum line pockets. The particular size of the flexible member can be optimized to produce effective acoustic cleaning with the fluid jet.

Figure 9:
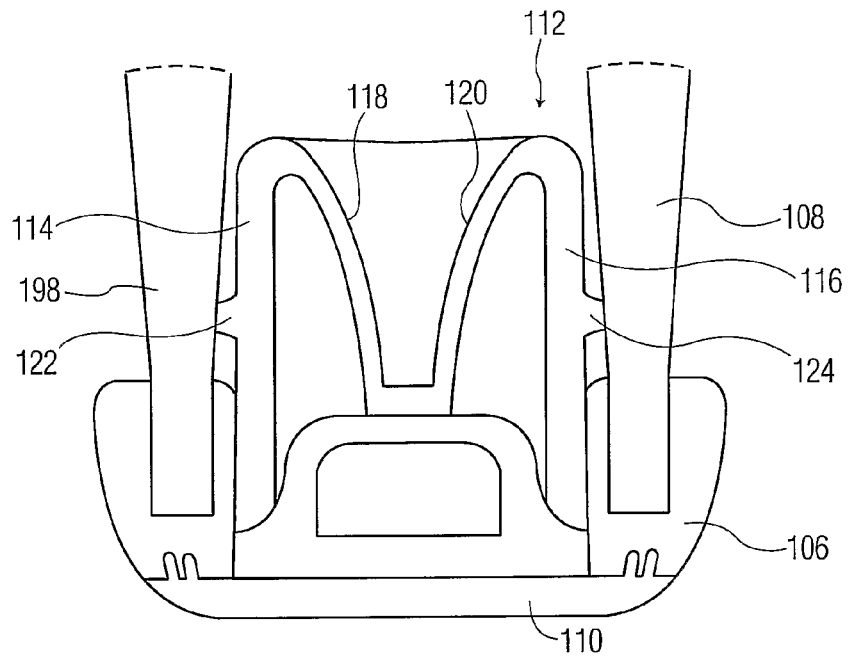
FIG. 9 is a cross-sectional view of a variation of the embodiment of FIGS. 6-8.

FIG. 9 is a variation of the embodiment of FIGS. 6-8. It includes a brush holder member 106 in which are stapled conventional bristle tufts 108. The bristle holder member 106 is secured to a base overmold element 110. A flexible member/membrane 112, also generally in the shape of an "M", is mounted on the central portion of the brush holder member and extends lengthwise of the brush. Positioned longitudinally on the brush holder member at the center thereof is a support rib member 113. The outer portions 114 and 116 of the member are thicker than the internal portions 118 and 120, which extend from the top of the outer portions to rib 112.

On the exterior surface of the two outer portions 114 and 116 are projections 122 and 124 which extend outwardly therefrom. Projections 122 and 124 contact bristle tufts 108. In operation, the brush holder member does not move by virtue of the flexible member action; the bristle tufts 108 are, however, moved by outward action of the projections 122, 124 when outer portions 114 and 116 of the flexible member 112 move. Fluid is directed toward the teeth by action of the inner portions 118 and 120 of the flexible member, similar to the action of the embodiment of FIGS. 6-8.

Figure 10:
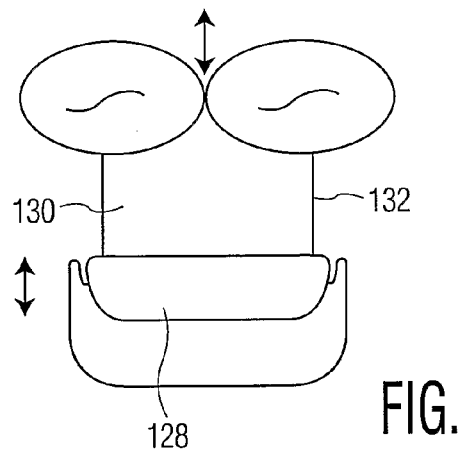
FIG. 10 is a cross-section of a further embodiment of the present invention.

FIG. 10 shows a further embodiment of the invention. This embodiment includes a flexible member 128 acting on a matrix 130, which in the embodiment shown is a sponge member. This embodiment is designed to clean complex teeth surfaces. In operation, pressure is applied to the member 128 by a conventional drive system (not shown), moving the member toward the teeth, compressing the sponge 130, with fluid exiting from the sponge and along the surfaces of the teeth and into the interproximal areas of the teeth to create a shear cleaning effect. The outer peripheral boundary 132 of the matrix sponge 130 is sealed to prevent fluid flow out of the matrix portion not in contact with the teeth.

The characteristics of the sponge restrict the flow of fluid and gas. It can thus transmit shear force to the complex surfaces of the teeth. Further, the direct contact of the matrix sponge member 130 with the surfaces of the teeth produces mechanical cleaning of the exposed surfaces of the teeth. Access to hard-to-reach areas with the fluid is achieved with the matrix. The sponge, because of its flexibility, may by application of pressure be brought into contact with some interdental space. The fluid shear cleaning, mechanical cleaning and transmission of force to the teeth surfaces produces a good cleaning of the teeth.

The material for the sponge is, for example, silicone, such as Silastic from Dow Corning. The porosity of the sponge material should be less than 80% open volume, but more than 50%. Below 50%, the sponge is too dense and unable to flex adequately to reach interdental areas. The openness of the cell structure should be greater than 50%, since below 50%, the fluid is not sufficiently impeded by the structure to produce efficient surface shear forces. The cell structure can be up to 100% closed.

Figure 11:
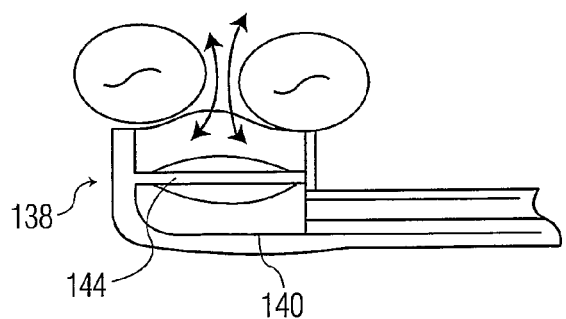
FIGS. 11-13 are cross-sectional views of variations of a still further embodiment of the present invention.

FIG. 11 shows another embodiment of the present invention involving a complex flexible member (membrane) structure 138. The membrane structure 138 is mounted on a toothbrush stem 140, which is a plastic or similar material. This arrangement of FIG. 11 does not include any bristles. Flexible member 138 includes an outer sealing portion 142 which extends around the periphery of the brushhead and is positioned against adjacent teeth to provide a sealing function for the fluid. The sealing portion 142 is preferably substantially continuous but may have breaks or spaces therein. A center portion 144 of the membrane 138 is driven to move generally toward and away from the teeth. The resulting fluid flow produces fluid motion and resulting cleansing of the teeth. The sealing portion 142 encloses an area on the teeth being cleaned and produces effective fluid flow dynamics and resulting cleaning.

Figure 12:
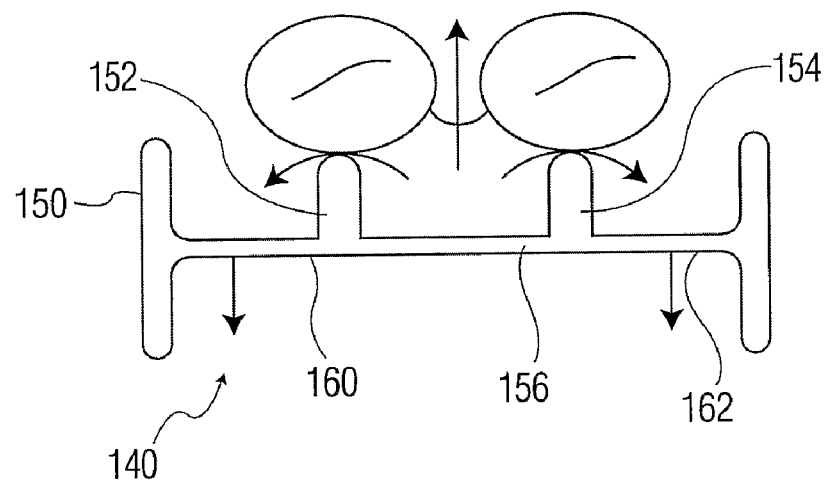

An alternative to the flexible member of FIG. 11 is shown in FIG. 12, involving a more complex flexible member/membrane 148, with an outer, substantially continuous sealing portion 150 and two spaced inner sealing ribs 152 and 154 which extend the width of the brushhead. Sealing ribs 152 and 154 are arranged and spaced to contact adjacent teeth. Movement of the flexible member 148, in response to a driving action, produces a complex fluid flow. Inner central section 156 moves toward the teeth, while outer central sections 160 and 162 move away from the teeth and vice versa. Fluid moves in shear across the face of the teeth as well as into the inter-proximal areas, as shown by the arrows in FIG. 12. This arrangement provides mechanical cleaning of the teeth as well as shear cleaning.

This operation of this embodiment is enhanced by a higher viscosity fluid, for example one-third toothpaste, with the remaining being saliva or water.

Figure 13:
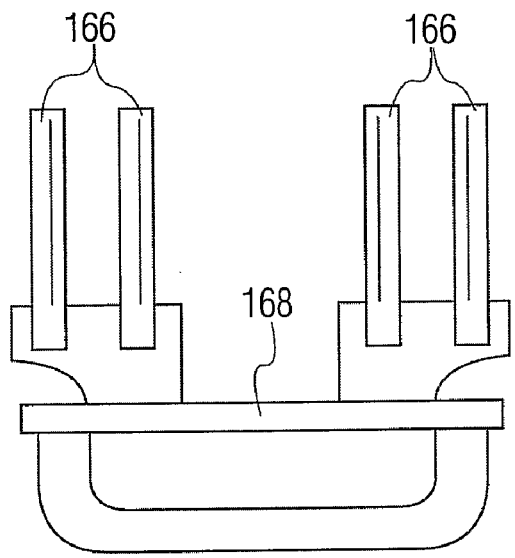

FIG. 13 shows a further variation of the embodiment of FIG. 11, using tufts of bristles 166 mounted to the outer portion (edge) of flexible member 168. When the flexible member 168 flexes in operation to produce fluid flow in the direction of the teeth, bristle tufts 166 in the flexible member (membrane) move outward producing a mechanical cleansing action on the teeth, in addition to the acoustic cleaning by action of the fluid caused by movement of the membrane.

The embodiments of FIGS. 11 or 12 can be combined with FIG. 13 to produce bristle motion inward while the central section of the flexible member moves toward the teeth.

In summary, the flexible member (membrane) assembly, specifically the flexible membrane portion of the assembly, will move at a frequency within the range of 30-700 Hz, with an amplitude of the 0.5 to 5 millimeters in one direction, for example, 5 millimeters from a rest position toward the teeth and then 5 millimeters back to the rest position. The flexible membrane can be driven with signal waveforms of various shapes, including sinusoidal and sawtooth, which in some cases may be preferred, but also including triangular, square wave, and other shapes. The system with its programmable capability can be used to match selected signal waveforms with selected areas of the mouth during a brushing event or events.

As briefly discussed above, the membrane may be partially surrounded by a wall element which serves as a boundary for fluid action as it comes into contact with the teeth. A range of distance from the top of the membrane to the top of the surrounding (or partially surrounding) wall element can vary from 2 millimeters to 8 millimeters. When the top edge of the boundary wall is positioned against the teeth, the membrane is positioned a fixed distance away from the teeth, improving the consistency of cleaning, particularly in interproximal (interdental) areas.

The shape of the membrane may also be significant. In many cases, a circular membrane is effective but other shapes are effective as well, including oval and rectangular, with the rectangular configuration being typically rounded at the corners. The length of such a membrane can vary from 10 to 25 millimeters. Typically, one membrane will be used, although in many situations, more than one membrane, i.e. one, two or three separate membranes, will be effective.

Still further, the driving signal may include one or multiple harmonics, including, for instance, three harmonics of the fundamental frequency.

The assembly can be configured such that the flexible membrane (member) can move toward or away from the teeth, even at right angles to the teeth as discussed above, or at other angles relative to the teeth, including approximately parallel to the teeth. The action, however, must be such as to maintain the fluid dynamic action to remove biofilm from the teeth.

All of the above assist to various degrees in the cleaning of the teeth, including the interproximal and/or sub-gingival areas. The action of the flexible member (membrane) interacts with the fluid in the mouth to produce a fluid dynamic action in the vicinity of the teeth which results in sufficient shear pressure to surpass the threshold value necessary to remove biofilm from the teeth, as well as interproximal and sub-gingival areas. The fluid used in the mouth can be either compressible or noncompressible.

Accordingly, a new power toothbrush has been described which uses acoustic action produced by an acoustic action member, such as a flexible membrane, for example, a bellows-like member, to produce acoustic wave action in fluids in the mouth to in turn result in cleansing of the teeth through shear-type action against biofilms on the teeth, as well as interdentally and subgingivally. The cleansing effect is clinically significant, i.e. the results are substantially equivalent to or better than conventional commercial electric scrubbing toothbrushes, including removal of a substantial amount of biofilm. It has the advantage of virtually no tissue abrasion; and because it acts with a fluid foam medium, it has the advantage of reaching hard-to-reach places between the teeth and under the gum line. It thus produces effective cleansing action independent of scrubbing, although bristles can also be used and moved by action of the acoustic action membrane to enhance the overall cleansing action.

Although a preferred embodiment of the invention has been disclosed for purposes of illustration, it should be understood that various changes, modifications and substitutions may be incorporated into the embodiment without departing from the spirit of the invention which is defined by the claims which follow.

What is claimed is:

1. A power toothbrush, comprising:
   a handle portion;
   a brushhead portion, the brushhead portion including a flexible acoustic member for creating an acoustic wave effect on fluid in a user's mouth and a set of bristles which at least partially surround the periphery of the acoustic member, wherein the acoustic member is in the shape of an "M" having two opposing inner walls and two opposing outer walls; and
   a drive system for moving the acoustic member, such that the inner walls of the acoustic member move inwardly toward each other and then back to a rest position, wherein such movement of the inner walls produces fluid movement to the teeth, producing a cleansing effect on the teeth.

2. The power toothbrush of claim 1, wherein the brushhead portion includes a base member into which the acoustic member is mounted, the base member including an upstanding central rib to which lower ends of the inner walls of the acoustic member are secured.

3. The power toothbrush of claim 1, wherein movement of the acoustic member results in back and forth movement of the bristles for cleaning of the surfaces of the teeth.

4. The power toothbrush of claim 1, including outwardly directed projections on the outer walls of the acoustic member, such that movement of the acoustic member results in the projections moving the bristles.

5. The power toothbrush, comprising:
   a handle portion;
   a brushhead portion, the brushhead portion including a flexible acoustic member and a matrix member; and
   a drive system for moving the acoustic member toward the teeth, thereby applying pressure to the matrix member, compressing the matrix member such that fluid exits from the matrix member along the surfaces of the teeth into the interproximal areas of the teeth, creating a shear cleaning effect for the teeth, wherein the outer peripheral boundary of the matrix is sealed to prevent fluid flow out of the matrix member not in contact with the teeth.

6. The power toothbrush of claim 5, wherein the acoustic member includes a central portion which moves toward and away from the teeth and a pair of opposing upstanding rib portions on either side of the central portion which contact the teeth, providing a sealing effect for the fluid.

7. The power toothbrush of claim 6, including two additional upstanding rib portions outboard of the pair of rib portions, and two additional central portions between each additional rib portion and the pair of rib portions, wherein the additional rib portions move in a direction opposing the movement of the central portion.

8. The power toothbrush of claim 5, wherein the matrix member is a sponge, the sponge member having a porosity of 50% to 80% open volume and having an openness greater than 50%, wherein in operation, the sponge member is brought into contact with the teeth for cleaning.

9. A method for cleaning teeth with acoustic wave action, comprising the steps of:
   providing a fluid capable of transmitting acoustic waves in the mouth of a user;
   providing a hand-held power toothbrush which comprises: a hand-held handle portion; a head portion, the head portion being configured and adapted to be positionable in the mouth of the user for cleaning of teeth, the head portion containing a flexible diaphragm acoustic action member for creating sonic energy acoustic wave action away from the head portion, the acoustic wave action acting on the fluid in the user's mouth, wherein the flexible diaphragm includes a substantially flat front portion bounded by a peripheral edge portion; the power toothbrush further including an acoustic drive system for producing energy to move the acoustic action member relative to the teeth, at a frequency in the range of 30-700 Hz, to create a sonic frequency acoustic wave from or off of the acoustic action member, the movement of the acoustic action member having an amplitude in the range of 0.5-5 mm from a rest position, toward and away from the teeth of the user, wherein movement of the acoustic action member produces a fluid dynamic action with the fluid in the mouth, without contacting the teeth, sufficient to produce a value of shear stress on the teeth which is greater than the threshold to remove biofilm from the teeth.

10. The too method of claim 9, including a boundary wall element substantially surrounding the acoustic member, wherein the top of the boundary wall is approximately at least 2 millimeters above the top of the acoustic member.

11. The method of claim 9, wherein the acoustic member is driven by a waveform of selected configuration.

12. The method of claim 11, wherein the selected waveform configuration is sinusoidal.

13. The method of claim 11, wherein the selected waveform configuration is a sawtooth.

14. The method of claim 11, wherein the waveform includes at least one harmonic frequency.

15. The method of claim 9, wherein the toothbrush includes a programmable control system for operating the drive system with different waveforms, so that selected waveforms can be used on selected areas of the mouth.

* * * * *